US005792041A

United States Patent [19]
Kobayashi et al.

[11] Patent Number: 5,792,041
[45] Date of Patent: Aug. 11, 1998

[54] INFANT INCUBATOR

[75] Inventors: Shinichi Kobayashi, Tokyo; Toshiyuki Kamisawa, Urawa; Kazuo Matubara, Tokyo, all of Japan

[73] Assignee: Atom Medical Corporation, Bunkyo-Ku, Japan

[21] Appl. No.: 800,532

[22] Filed: Feb. 18, 1997

[30] Foreign Application Priority Data

Feb. 29, 1996 [JP] Japan ................... 8-069304

[51] Int. Cl.⁶ .................................. A61G 11/00
[52] U.S. Cl. ........................................ 600/22
[58] Field of Search ........................ 600/21, 22

[56] References Cited

U.S. PATENT DOCUMENTS

| | | | |
|---|---|---|---|
| 4,034,740 | 7/1977 | Atherton et al. | 600/22 |
| 4,697,193 | 9/1987 | Howkins | 346/1.1 |
| 5,316,542 | 5/1994 | Koch et al. | 600/22 |
| 5,415,618 | 5/1995 | Koch | 600/22 |
| 5,539,854 | 7/1996 | Jones et al. | 600/22 |
| 5,616,115 | 4/1997 | Gloyd et al. | 600/22 |

FOREIGN PATENT DOCUMENTS

| | | |
|---|---|---|
| 4204398 C1 | 6/1993 | Germany . |
| 7-328077 | 12/1995 | Japan . |
| 8-679 | 1/1996 | Japan . |
| WO 93/16671 | 9/1993 | WIPO . |

*Primary Examiner*—Jennifer Bahr
*Assistant Examiner*—Samuel Gilbert
*Attorney, Agent, or Firm*—Woodcock Washburn Kurtz Mackiewicz & Norris LLP

[57] ABSTRACT

An infant incubator having a base (3) for supporting a premature baby; a hood (7) mounted on the base (3) to provide an incubation chamber (9) isolated from the atmosphere; a first duct (19) having a fan for circulating inner air through the incubation chamber (9); and a first heater (47) disposed on said first duct to provide a heated air; a second duct (21) branched from the first duct (19), and having a detachable humidifying vessel (15) for storing the water and combined through a shutter compartment (53) to the first duct (19) downstream of the humidifying vessel (15); a second heater (37) for heating the humidifying vessel (15); a first temperature sensor (57) to measure a chamber temperature in the incubation chamber; a second temperature sensor (39) to measure a water temperature in the humidifying vessel (15); and MPU (55) for controlling the second heater (37) based on the chamber temperature by the first temperature sensor (57) and the water temperature. The shutter compartment (53) is controlled to be moved by the predetermined amount associated with the second heater (37) being controlled to set the current water temperature to the predetermined water temperature in a lookup table, and when the vessel temperature gradually comes close to the predetermined vessel temperature, the mixing ratio is returned to the default ratio.

4 Claims, 4 Drawing Sheets

| CHAMBER TEMPERATURE | VESSEL TEMPERATURE |
|---|---|
| < 30 °C | 33 °C |
| 30 ~ 32 °C | 34 °C |
| 32 ~ 34 °C | 36 °C |
| 34 ~ 36 °C | 39 °C |
| 36 ~ 38 °C | 44 °C |
| > 38 °C | 46 °C |

1

INFANT INCUBATOR

BACKGROUND

The present invention relates to an infant incubator having dual circulating-air ducts, in which a premature baby is protectively received in an incubation chamber under a controlled temperature and humidity.

An infant incubator is utilized to nurse a premature baby having physical weakness in an optimal environment isolated from the atmosphere. In the infant incubator, outer air is introduced and purified through a ventilation mechanism to an incubation chamber which receives the premature baby, and inner air is circulated through the incubation chamber, while maintaining a desirable temperature, and if necessary, humidity in the incubation chamber.

In prior art, only a circulating-air duct for humidifying the inner air is provided under the incubation chamber as described in JP-A-7-507,216 claiming priority of U.S. Ser. No. 842,455 dated Feb. 27, 1992, via a PCT route; and JP-B-7-108,310 claiming priority of DE P42 04 398.0 dated Feb. 14, 1992, respectively. However, it is difficult to rapidly control the humidity, particularly from the higher level to the lower destination level because of lower response time of the humidity control in the circulating-air duct contacting the water.

JP-A-7-328,077 and JP-A-8-679, each claiming priority of U.S. Ser. Nos. 259,829, now abandoned in favor of U.S. Pat. Nos. 5,616,115, and 260,855, respectively, and dated Jun. 15, 1994, disclose dual circulating-air ducts with two interconnection ports between which a heater and a fan for heating and circulating the mixed air are disposed. These documents also disclose a heat-exchanger having thermal conductive fins partially impregnated with the water of a humidifying vessel. The humidifying vessel can not be essentially removed from the infant incubator.

To improve the response time of the humidity control, the present applicant or assignee proposed controllable dual circulating-air ducts wherein a branch or interconnection port is disposed downstream of a heater and fan for heating and circulating the inner air, with JP-Y-2-38736 and JP-Y-2-38737 both granted and issued on Oct. 18, 1990. These documents, as means for humidifying the inner air, disclose a first duct for bypassing the heated circulating air through a heater, a second duct branched from the first duct and having a detachable humidifying vessel for storing the water to provide a humidifying air by contacting the heated circulating air with the water in the humidifying vessel, and means for mixing the humidifying air and the heated circulating air at the conventional ratio. However, there are no means to control the conventional ratio.

A chamber temperature in the incubation chamber may be adjusted to an arbitrary temperature between 25° C. and 38° C. by controlling the heater for heating the circulated inner air by monitoring the chamber temperature. The humidity in the incubation chamber is also desirably set an arbitrary humidity within the range of 20% to 80%.

However, even when the heating of the water is stopped, the vessel temperature does not suddenly decrease, and the steam is still generated in minute amounts. Accordingly, when the chamber temperature exceeds a predetermined level or the humidity in the incubation chamber exceeds a predetermined level, a long time is necessitated until the vessel temperature is decreased. During this period, adjustment of the humidity in the incubation chamber is impossible.

SUMMARY OF THE INVENTION

It is an object of the present invention to provide an infant incubator in which a chamber temperature is precisely controlled while the ability for humidifying the incubation chamber is ensured in some content.

According to the present invention, an infant incubator comprises: a base for supporting a premature baby; a hood mounted on the base to provide an incubation chamber isolated from the atmosphere; a first duct having a fan for circulating an inner air through the incubation chamber; a first heater disposed on the first duct to provide a heated air; a second duct branched from the first duct downstream of the first heater, having a detachable humidifying vessel for storing the water and combined through a shutter compartment to the first duct downstream of the humidifying vessel; a second heater for heating the humidifying vessel; a first temperature sensor to measure a chamber temperature in the incubation chamber; a second temperature sensor to measure a water temperature in the humidifying vessel; and means for controlling the second heater based on the chamber temperature by the first temperature sensor and the water temperature.

Alternatively, the shutter compartment is controlled to be moved by the predetermined amount associated with the second heater being controlled to set the current water temperature to the predetermined water temperature in a lookup table, and when the vessel temperature gradually comes close to the predetermined vessel temperature, the mixing ratio is returned to the default ratio.

BRIEF DESCRIPTION OF THE DRAWINGS

The foregoing and other objects, features and advantages of the invention will become more apparent upon a reading of the following detailed description and drawings, in which.

DETAILED DESCRIPTION OF THE PREFERRED EMBODIMENT

Figure 1:
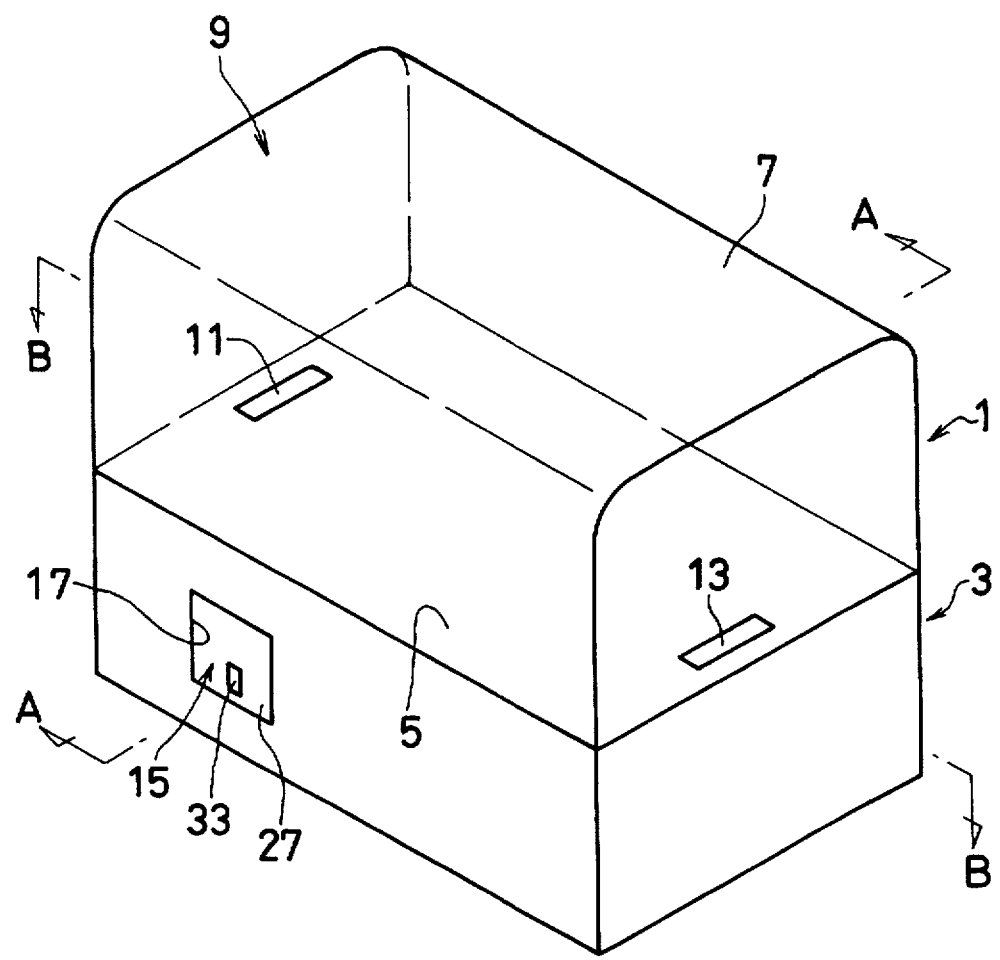
FIG.1 shows a schematic perspective view of an embodiment of an infant incubator according to the present invention.

FIG. 1 shows a schematic perspective view of an embodiment of an infant incubator 1 according to the present invention. The infant incubator 1 comprises a base 3 having an upper plate 5 pivotally covered with a transparent hood 7 to provide the space as an incubation chamber 9 to receive a premature baby. The transparent hood 7 is pivotally and sealingly mounted on the upper plate 5 of the base 3 at its back side. Output opening 11 and input opening 13 are provided with the upper plate 5 of the base 3 to circulate through the incubation chamber 9 a mixing gas or air being controlled at the desirable temperature and humidity. A drawer type humidifying vessel or tray 15 is detachably mounted to a front face of the base 3.

Figure 2:
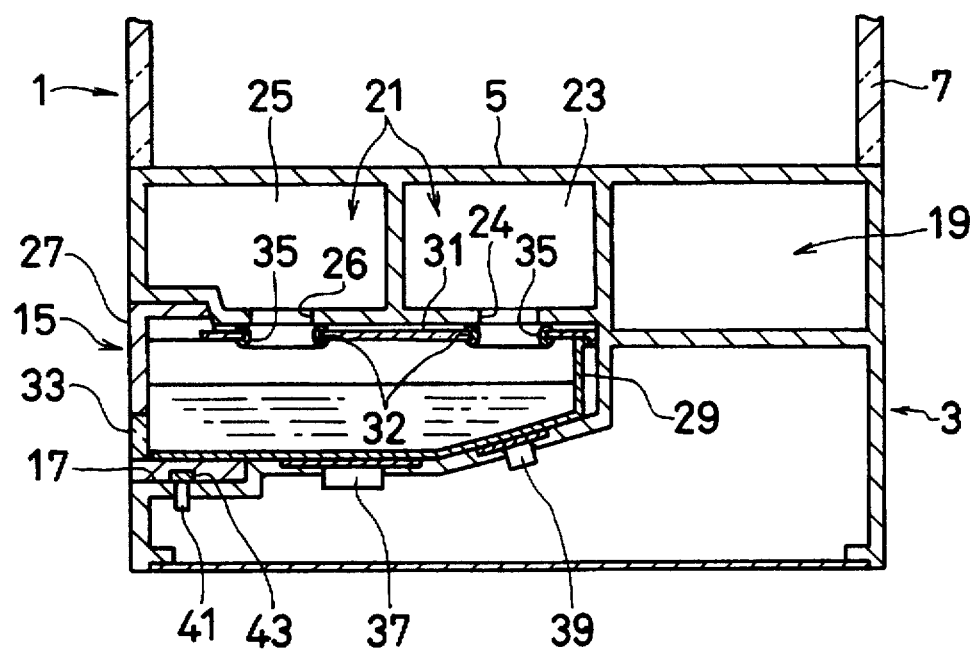
FIG. 2 shows a partial cross sectional view of the infant incubator taken in line A—A of FIG. 1.

FIG. 2 shows a partial cross sectional view of the infant incubator 1 taken in line A—A of FIG. 1. Inside the base 3, a support portion 17 for the humidifying vessel 15 is provided as well as a first duct 19 without any humidifying vessel and a second duct 21. The first and second ducts 19 and 21 are disposed under the incubation chamber 9 above an open space for receiving the humidifying vessel 15. The second duct 21 comprises an input side duct 23 for inputting the heated air to the humidifying vessel 15 through an opening 24 and an output side duct 25 for outputting the humidifying air from the humidifying vessel 15 through an opening 26.

The humidifying vessel 15 mainly comprises an outer panel portion 27 disposed at a front side of the base 3, a dam portion 29 for storing water, and a cap plate 31 for covering the upper side of the dam portion 29. A transparent window 33 is provided with the outer panel portion 27 to monitor the water level of the dam portion 29. The dam portion 29 is made of aluminum and has a liner of polytetrafluoroethylene resin coating so called a Teflon coating inside thereof and an anodized aluminum processing outside thereof.

Accordingly, even if impurities such as calcium components are precipitated in the dam portion 29 by using water containing impurities, the precipitation will not adhere inside thereof for easy clean-up or sterilization of the dam portion. The outside of the humidifying vessel 15 is also anodized to prevent the outside thereof from sustaining damage or rusting. Two openings 32 corresponding or aligning to the openings 24 and 26 of the input and output side ducts 23 and 24 are provided with the cap plate 31. Seal members 35, 35, such as rubber rims, are attached to the openings 32, 32 to prevent the unprocessed and humidifying air from leaking, respectively when the humidifying vessel 15 is mounted to the support portion 17.

The support portion 17 comprises a heater 37 for heating the humidifying vessel 15, a vessel temperature sensor 39 for measuring temperature of the humidifying vessel 15, and a mounting sensor 41 for detecting the mounting of the humidifying vessel 15. The heater 37 contains, for example, a ceramic heater so as not to generate excessive heat. The humidifying vessel temperature sensor 39 contains, for example, a thermistor contacting the bottom of the humidifying vessel 15 urged by a spring (not shown). The mounting sensor 41 contains, for example, a Hall effect device to indirectly detect the mounting of the humidity vessel 15. Therefore, a magnet 43 is embedded in the predetermined position of the outer panel portion 27 of the humidifying vessel 15 so that the magnet 43 meets the Hall effect device upon mounting the humidifying vessel 15.

Figure 3:
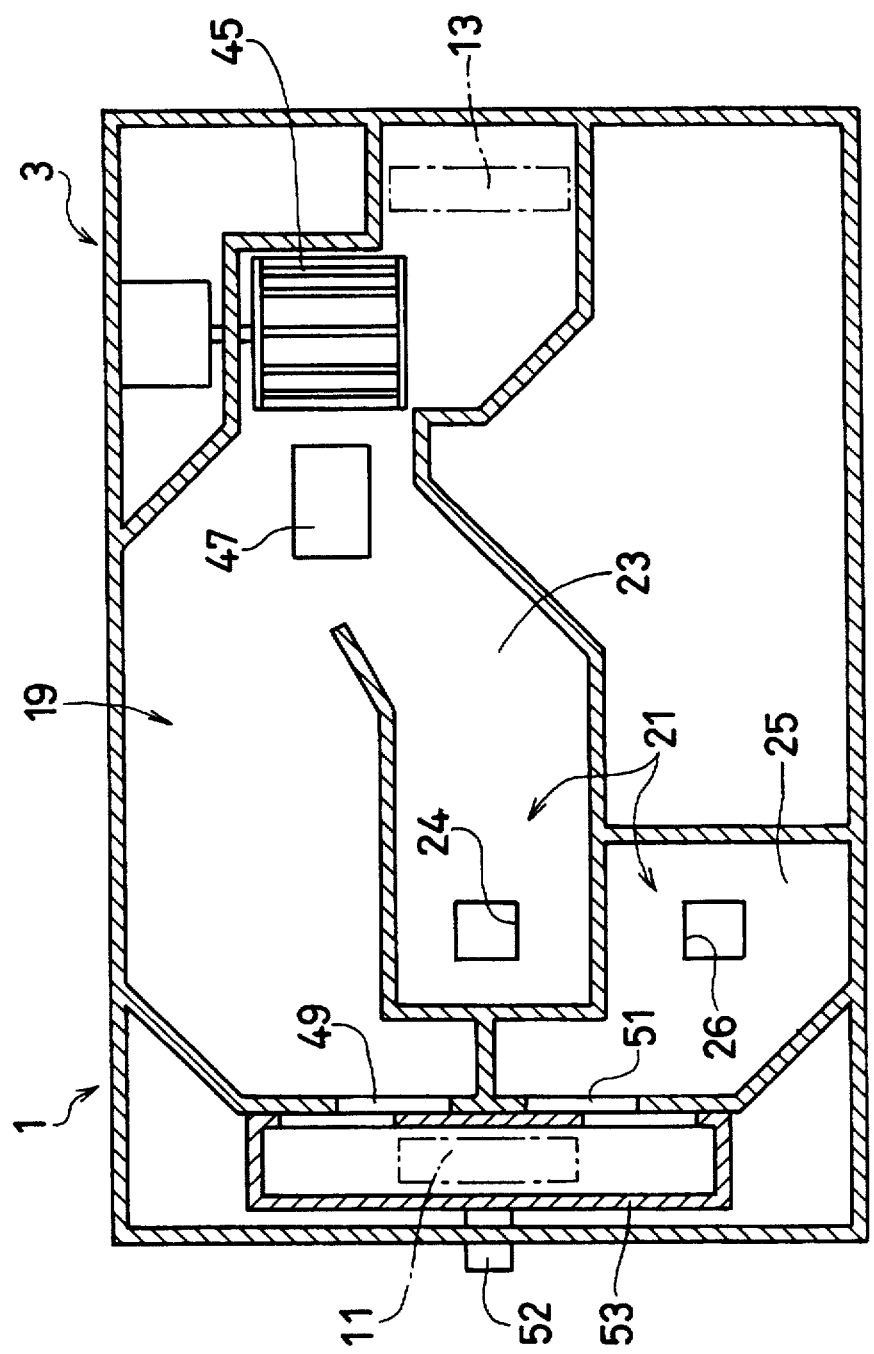
FIG. 3 hows a partial cross sectional view of the infant incubator taken in line B—B of FIG. 1.

FIG. 3 shows a partial cross sectional view of the infant incubator taken in line B—B of FIG. 1. In FIGS. 2 and 3, similar or the same members corresponding to those of FIG. 1 are denoted with the same numerals, respectively.

In FIG. 3, the upper plate 5 partitions the incubation chamber 9 and the first duct 19 and has the output opening 11 and the input opening 13 as shown in phantom lines. A fan 45 for circulating the inner air through the incubation chamber 9 is disposed on the first duct 19 adjacent to the input opening 13. Downstream of the fan 45, a heater 47 is also provided on the first duct 19 to heat the inner air.

Downstream of the heater 47, a second duct 21, branched from the first duct 19, is provided so that the heated circulating air, passing through the first duct 19, is directed to the output opening 11 through a first exit 49. Meanwhile the humidified air passing through the second duct 21 is passed through the humidifying vessel 15 (FIG. 2) to humidify the heated air and is then directed to the output opening 11 through a second exit 51. The flow rate passing through the first and second exits 49 and 51 is adjusted by a shutter compartment 53 so that the humidifying air and the heated circulating air are mixed in a predetermined ratio and supplied to the incubation chamber 9 through the output opening 11.

The shutter compartment 53 is slidably moved back and forth by a manual knob 52 or an electric motor having a rack and pinion mechanisms so that the aperture degrees of the respective exits 49 and 50 are quickly adjusted while the sum of their aperture sizes are constant. By changing the mixing ratio of the heated and humidifying airs from the respective exits 49 and 51, the humidity of the inner air circulating through the incubation chamber may be quickly adjusted. However, the mixing ratio is assumed to be 1:1 to simplify the following descriptions. Therefore, the air mixing ratio may correspond or be proportional to the offset of the movable shutter compartment 53, and the offset is converted to an electric signal through a linear or rotary potentiometer or encoder 54 (FIG. 4).

Figures 4, 5:
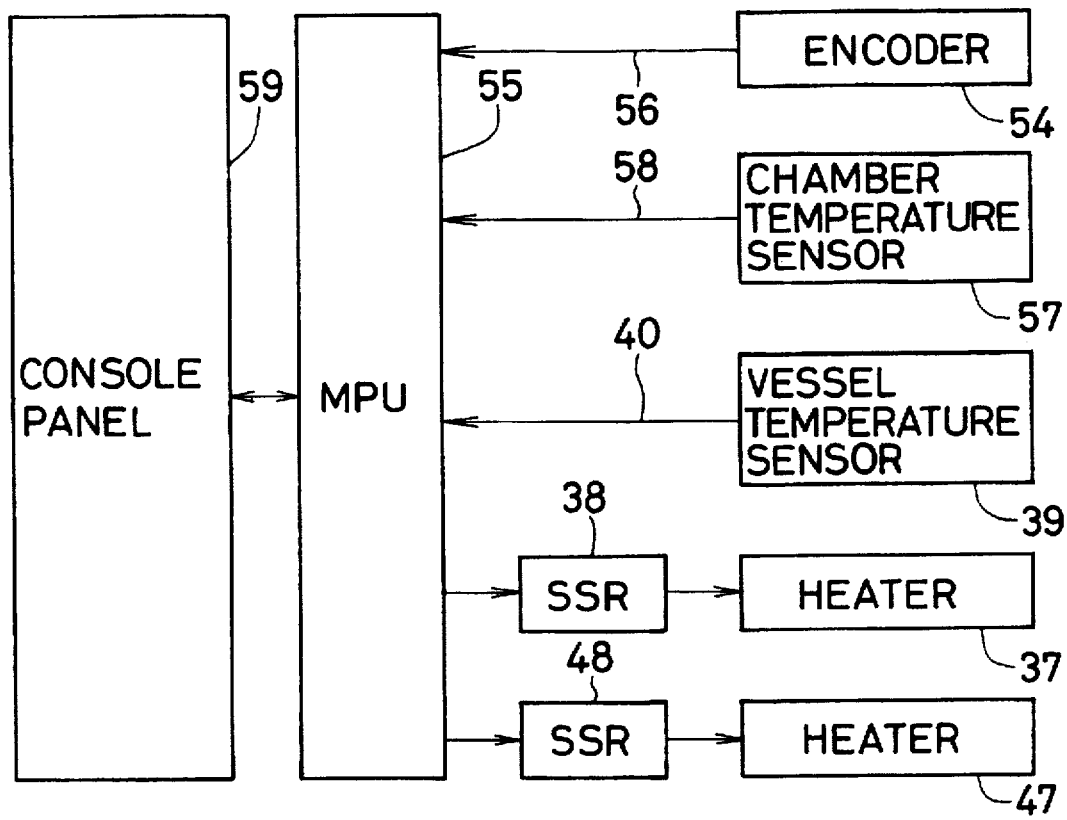
FIG. 4 shows a control block with respect to humidifying vessel of the infant incubator according to the present invention.
FIG. 5 rows a lookup table stored in ROM or RAM in a one-chip MPU shown in FIG. 4.

FIG. 4 shows a control block with respect to humidifying vessel of the infant incubator according to the present invention. In FIG. 4, MPU 55 contains a one-chip microcomputer H8/532 commercially available from Hitachi Corporation, Japan and includes 32 k byte ROM, 1 k byte RAM and 8 channels 10 bit A/D converter. The A/D converter includes 8 selectable analog inputs interfaced to several sensors with or without preamplifiers.

An incubation chamber temperature sensor 57, disposed in the incubation chamber 9, and the humidifying vessel temperature sensor 39 have output signals 58 and 40 each supplied to the MPU 55 through the channels of the A/D converter (not shown) as well as a digital output signal 56 from the encoder 54 or an analog output signal from the potentiometer through the A/D converter.

As is well known those skilled in the art, the humidity in the environment is determined by levels of dry and wet thermometers. Then, the MPU 55 comprises an internal ROM for storing a subroutine program to control the heater 37 for heating the humidifying vessel 15 through a Solid State Rely (SSR) 38 in view of the humidifying vessel output signal 40 so that the vessel temperature is settled to a predetermined vessel temperature defined by a preset humidity.

The internal ROM in the MPU also stores another subroutine program to control the heater 47 for heating the inner air circulated therethrough via another SSR 48 in view of the chamber output signal 58 so that chamber temperature is settled to a preset chamber temperature.

When the humidity and temperature in the incubation chamber 9 are preset by a ten-key (not shown) on a console panel 59 and monitored by a LED display (not shown) thereof, the MPU 55 will control the heater 47 to converge the chamber temperature to the preset chamber temperature and then or simultaneously turn on or off the heater 37 to converge the humidifying vessel temperature to the predetermined vessel temperature based on the preset humidity by the ten key.

If the preset humidity or predetermined vessel temperature is lower than the current humidity or vessel temperature, the heater 37 and mixing ratio are controlled to be turned off and to decrease the flow rate of the humidifying air based on the difference between the preset and current humidities, respectively. If the preset humidity or predetermined vessel temperature is higher than the current humidity or vessel temperature, the heater 37 and mixing ratio are controlled to be turned on and to increase the flow rate of the humidifying air based on the difference therebetween. Therefore, the shutter compartment 53 is slidably driven by the desirable offset with the electric motor controlled by the MPU 55. The heater 37 is then controlled to be turned on or off to set the current water temperature to the predetermined water temperature in a lookup table. When the current humidity or vessel temperature gradually comes close to the preset humidity or predetermined vessel temperature, the mixing ratio is returned to the default ratio, for example, 1:1 by moving the shutter compartment 53 by the electric motor.

The MPU also controls the fan 45 (FIG. 3) to maintain the predetermined flow rate of the circulated inner air and recognizes the opening ratio or aperture degrees of the respective exits 49 and 50. The consol panel 59 also monitors the operation of the MPU 55 and carries out a preferable process such as the stoppage of the MPU 55 operation when a malfunction of the MPU 55 is detected by a watch dog timer (not shown).

FIG. 5 shows a lookup table showing relations between predetermined chamber and vessel temperatures at the preset humidity value and stored in the internal ROM or RAM in the one-chip MPU system shown in FIG. 4. In FIG. 5, the relations between predetermined chamber and vessel temperatures at the preset humidity values to be stored in the internal ROM or RAM are calibrated by measuring the real chamber temperatures and humidities, and the real vessel temperatures. In practice, when a certain chamber temperature is preset and the humidifying vessel is heated to increase its water temperature, the upper limit of the water temperature which cause the chamber temperature not to increase is measured to relate the water temperature with the chamber temperature. If the chamber temperature and the water temperature are retained by the relation defined by the lookup table, the chamber temperature is accurately controlled by adjusting the output of the heater 47 (FIG. 3) for heating the circulated inner air without being effected by the chamber temperature of a vapor generated from the humidifying vessel. For example, the chamber temperature is a range between 32° C. and 34° C., the output of the heater 37 for humidifying vessel are controlled to make the maximum water temperature to be 36° C.

While the embodiments of the infant incubators according to the present invention are described as mentioned above, any modification to the shape and circuit construction thereof can be made. For example, the heater for heating the humidifying vessel may use a semiconductor device such as a Peltier element as well as the ceramic heater such as a Posistor. By using the Peltier element, as the humidifying vessel can be cooled or heated, the vapor is quickly diminished by cooling the humidifying vessel when the humidity of the incubation chamber is too high.

In this embodiment of the invention, although the surface temperature of the humidifying vessel is measured, the water temperature in the humidifying vessel may be directly measured.

According to the infant incubator of the present invention, the humidity of the incubation chamber can be easily determined by the chamber and vessel temperatures. The chamber temperature in the incubation chamber can be accurately controlled despite easily evaporating by heating the humidifying vessel.

The vapor is not leaked from the humidifying vessel to the receiving space of the base as the humidifying vessel is firmly mounted to the receiving space and then the power supply to the heater is energized. Even if the power supply to the heater is performed, the power supply to the heater is shut off when the humidifying vessel is removed from the base. Then, the heater does not extremely heat itself and the receiving space.

Further, the humidifying vessel can be easily cleaned up or sterilized by providing a liner resin having heat-tolerant, anti-chemical and hydrophobic characteristics even if water containing impurities is used.

The foregoing disclosure and description of the invention are illustrative and explanatory thereof, various changes in the size, shape, materials, components, as well as in the details of the illustrated construction and method of operation may be made without departing from the spirit of the invention.

What is claimed is:

1. An infant incubator, comprising:

a base for supporting a premature baby;

a hood mounted on the base to provide an incubation chamber isolated from the atmosphere;

a first duct having a fan for circulating inner air through said incubation chamber;

a first heater disposed on said first duct to provide heated air;

a second duct branched from said first duct downstream of said first heater, and having a detachable humidifying vessel for storing the water and combined through a shutter compartment to said first duct downstream of the humidifying vessel;

a second heater for heating the humidifying vessel;

a first temperature sensor to measure a chamber temperature in the incubation chamber;

a second temperature sensor to measure a water temperature in the humidifying vessel; and control means for controlling the second heater based on said chamber temperature measured by the first temperature sensor and said water temperature.

2. An infant incubator according to claim 1, wherein said second heater is energized when said humidifying vessel is mounted to a predetermined position in said second air duct.

3. An infant incubator according to claim 2, wherein said humidifying vessel is lined by at least one of a heat-tolerant and hydrophobic coating on an inner surface thereof.

4. An infant incubator according to claim 1, wherein said shutter compartment is controlled to be moved by the predetermined amount associated with said second heater being controlled to set the current water temperature to the predetermined water temperature in a lookup table, and when said vessel temperature gradually comes close to said predetermined vessel temperature, a mixing ratio between said heated air and a humidifying air is returned to a default ratio.

* * * * *